United States Patent [19]

Yokoyama et al.

[11] Patent Number: 4,511,550

[45] Date of Patent: Apr. 16, 1985

[54] 1-(P-SUBSTITUTED OR UNSUBSTITUTED AMINOALKYL)PHENYLPROPANE-1,2-DIONE BIS(THIOSEMICARBAZONE) DERIVATIVES, AND THEIR PRODUCTION AND USE

[75] Inventors: Akira Yokoyama, Otsu; Yasushi Arano, Uji; Takeo Hosotani, Kyoto, all of Japan

[73] Assignee: Nihon Medi-Physics Co., Ltd., Hyogo, Japan

[21] Appl. No.: 438,776

[22] Filed: Nov. 3, 1982

[30] Foreign Application Priority Data

Sep. 7, 1982 [JP] Japan ................................. 57-155627
Sep. 7, 1982 [JP] Japan ................................. 57-155628
Sep. 8, 1982 [JP] Japan ................................. 57-157372

[51] Int. Cl.³ ...................... A61K 43/00; A61K 49/00
[52] U.S. Cl. ............................... 424/1.1; 260/112 R; 260/112 B; 424/9; 564/20
[58] Field of Search ................ 562/556; 424/323, 1.1, 424/9; 564/20; 260/112 R, 112 B

[56] References Cited

U.S. PATENT DOCUMENTS

| 3,382,275 | 5/1968 | Barrett | 564/20 |
| 3,709,935 | 1/1973 | Barrett | 564/20 |
| 3,824,276 | 7/1974 | Murray et al. | 564/20 |
| 4,287,362 | 9/1981 | Yokoyama et al. | 424/1.1 |
| 4,338,248 | 7/1982 | Yokoyama et al. | 424/1.1 |

FOREIGN PATENT DOCUMENTS

| 54920 | 6/1982 | European Pat. Off. | 424/1.1 |
| 74429 | 3/1983 | European Pat. Off. | 424/1.1 |
| 966849 | 8/1964 | United Kingdom | 424/323 |
| 0356274 | 11/1972 | U.S.S.R. | 564/19 |

OTHER PUBLICATIONS

Yokoyama et al., Chemical Abstracts, vol. 85, (1976) #139238g.

Primary Examiner—Christine M. Nucker
Attorney, Agent, or Firm—Birch, Stewart, Kolasch & Birch

[57] ABSTRACT

A radioactive diagnostic agent which comprises a physiologically active substance and a radioactive metallic element combined with a compound of the formula:

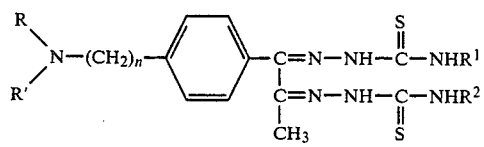

wherein $R$, $R'$, $R^1$ and $R^2$ are each a hydrogen atom or a $C_1$-$C_3$ alkyl group and n is an integer of 0 to 3. The agent is characteristic in having a high stability even after being administered into a human body and showing the substantially the same behavior as the physiologically active substance itself in a human body.

35 Claims, No Drawings

1-(P-SUBSTITUTED OR UNSUBSTITUTED AMINOALKYL)PHENYLPROPANE-1,2-DIONE BIS(THIOSEMICARBAZONE) DERIVATIVES, AND THEIR PRODUCTION AND USE

The present invention relates to 1-(p-substituted or unsubstituted aminoalkyl)phenylpropane-1,2-dione bis(thiocarbazone) derivatives (hereinafter referred to as "AAPT"), and their production and use. More particularly, it relates to AAPT of the formula:

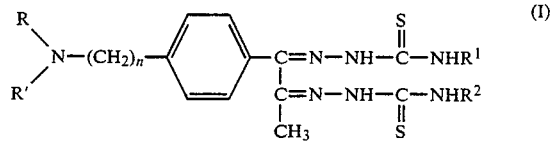

wherein R, R', $R^1$ and $R^2$ are each a hydrogen atom or a $C_1$-$C_3$ alkyl group and n is an integer of 0 to 3, their production process and their use as a carrier for a radioactive metallic element as well as a physiologically active substance.

For the purpose of a non-invading nuclear medical diagnosis such as recording, dynamic study and quantitative measurement of the blood circulation system, detection of physiological abnormality or localization of abnormality by imaging, there have been widely used physiologically active substances labeled with iodine-131 ($^{131}$I) such as $^{131}$I-labeled serum albumin and $^{131}$I-labeled fibrinogen. However, $^{131}$I has a long half life of about 8 days and emits beta-rays so that the patient administered therewith is exposed to a large quantity of radiation.

In order to overcome the said drawback in the $^{131}$I-labeled physiologically active substances, attempts have been made to provide radioactive diagnostic agents comprising physiologically active substances and radioactive metallic elements having more favorable physical properties than iodine-131 combined thereto. Among such attempts, there is known a labeling method wherein a physiologically active substance is treated directly with a radioactive metal salt to make a chelate compound, which may be used as a radioactive diagnostic agent. For instance, human serum albumin is treated with an aqueous solution containing technetium-99m ($^{99m}$Tc) in the form of pertechnetate in the presence of a reducing agent to give $^{99m}$Tc-labeled human serum albumin. Further, for instance, bleomycin is treated with an aqueous solution containing indium-111 ($^{111}$In) in the form of indium chloride to give $^{111}$In-labeled bleomycin. However, the chelate forming property of those physiologically active substances is not sufficient, and the once formed chelating bond is readily broken. In fact, $^{99m}$Tc-labeled serum albumin and $^{111}$In-labeled bleomycin are low in the stability after administration into living bodies. Thus, when they are administered to living bodies, $^{99m}$Tc and $^{111}$In are liberated quickly so that the behavior of the radioactivity in such bodies does not coincide with that of serum albumin or bleomycin as the physiologically active substance. This is a fatal defect for the nuclear medical diagnosis based on the exact trace of the behavior of the radioactivity which should coincide with the behavior of the physiologically active substance.

The present inventors proposed previously the use of 3-oxybutyralcarboxylic acid bis(4-methylthiosemicabazone) as a chelating agent which can be combined to a physiologically active substance (Japanese Patent Publn. (unexamined) No. 34664/1981). However, the terminal group in the above compound is a carboxyl group which can be combined to a physiologically active substance only by an amido bondage, and therefore the usage is limited. The present inventors also proposed the use of 3-aminomethylene-2,4-pentanedione bis(4-alkylthiosemicabazone) (Japanese Patent Publn. (unexamined) No. 102860/1982). However, the terminal amino group in this compound is located on the unsaturated carbon atom which lowers the electron density on the amino nitrogen atom and, as a result, injures the reactivity.

As a result of the extensive study, it has now been found that the AAPT (I) has a strong chelate-forming property and can be bonded to an amino group and/or a carboxyl group in physiologically active substances under a mild condition. It has also been found that a chemical product comprising a metallic element bonded to the AAPT (I) is sufficiently stable in living bodies. It has further been found that a chemical product comprising a physiologically active substance and a radioactive metallic element bonded thereto with intervention of the AAPT (I) is sufficiently stable in living bodies, and the behavior of the radioactivity in living bodies is quite coincident with that of the physiologically active substance itself.

According to the present invention, there is provided the AAPT (I), which is useful as a chemical carrier for a physiologically active substance and/or a radioactive metallic element. There is also provided the radioactive metallic element-combined compound comprising the AAPT (I) and a radioactive metallic element chelated thereto, which is useful as a radioactive diagnostic agent. There is further provided the physiologically active substance-combined AAPT (I) comprising the AAPT (I) and a physiologically active substance chemically bonded thereto with or without intervention of any linking aid, which is useful as a non-radioactive carrier to be used in diagnosis in nuclear medicine. There is still further provided the radioactive metallic element-labeled, physiologically active substance-combined AAPT (I) comprising the physiologically active substance-combined AAPT (I) and a radioactive metallic element chelated thereto, which is useful as a radioactive diagnostic agent.

The AAPT (I) is novel and can be prepared by condensing an oxime of a compound of the formula:

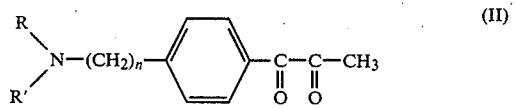

wherein R and R' are each as defined above with 4-$R^3$-thiosemicarbazide in which $R^3$ is $R^1$ or $R^2$.

The oxime wherein R and R' are each a $C_1$-$C_3$ alkyl group can be obtained by the following process:

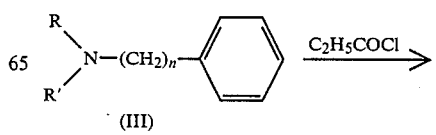

-continued

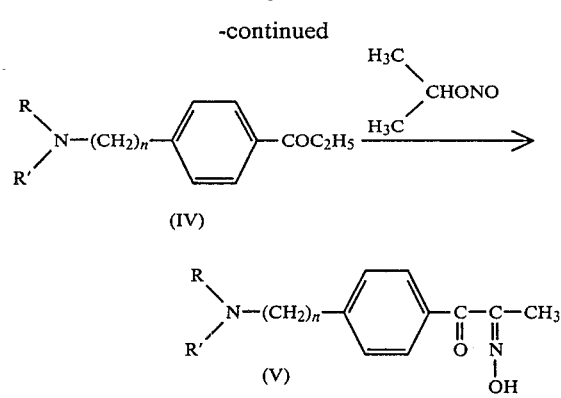

In the above process, the compound (III) is C-acylated with propionyl chloride according to a known method (Yu V Markova: Chem.Abst., 63, 17951f (1965)) to give the compound (IV), which is nitrosated with isopropyl or isoamyl nitrite in a per se conventional manner (Nathan Levin et al.: Org.Syn.Coll., Vol. 3, 191 (1955)) to give the oxime (V).

The oxime wherein R and R' are each a hydrogen atom can be obtained by the following process:

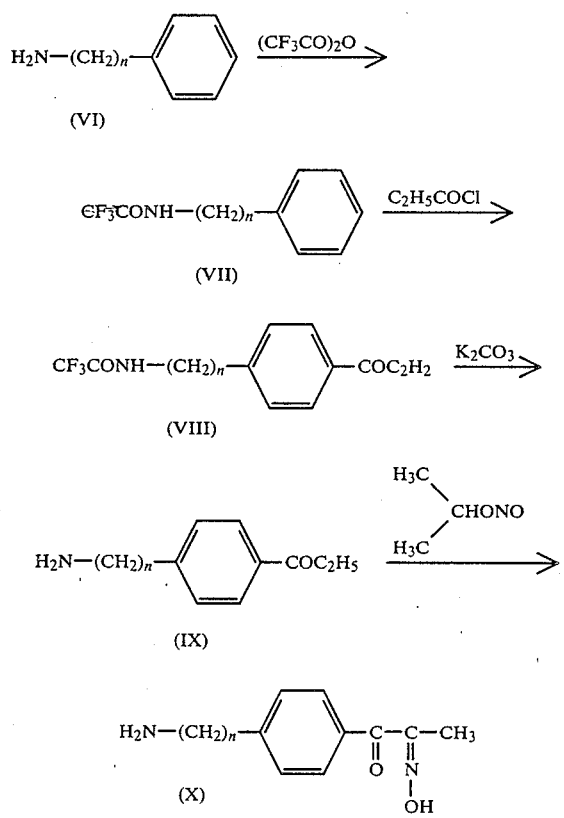

In the above process, the compound (VI) is N-acylated with a trifluoroacetylating agent to give the N-protected compound (VII), which is C-acylated in a manner similar to that in the C-acylation of the dialkylamino compound (III). The obtained compound (VIII) is subjected to removal of N-protective group following the method of Haward Newman (J.Org.Chem., 30, 1287 (1965)) to give the compound (IX), which is nitrosated in the same manner as that in the nitrosation of the dialkylamino compound (IV) to obtain the oxime (X).

The condensation of the oxime of the compound (II) with 4-$R^3$-thiosemicarbazide may be carried out in a single step or in two steps. When the AAPT (I) wherein $R^1$ and $R^2$ are same is to be produced, the condensation is usually carried out in a single step by reacting the oxime of the compound (II) with 4-$R^3$-thiosemicarbazide in a molar proportion of 1:2 or more. When the AAPT (I) wherein $R^1$ and $R^2$ are different is to be produced, the condensation is ordinarily carried out in two steps by reacting the oxime of the compound (II) with 4-$R^1$- or 4-$R^2$-thiosemicarbazide in a nearly equimolar proportion and then reacting the resultant monothiosemicarbazone with 4-$R^2$- or 4-$R^1$-thiosemicarbazide in a nearly equimolar proportion. In general, the condensation is effected in the presence of an acidic catalyst such as hydrochloric acid, hydrobromic acid or sulfuric acid, preferably in an inert solvent such as methanol or ethanol.

The AAPT (I) thus produced has two thiosemicarbazone groups which can catch a radioactive metallic element to form a chelate and an amino group which can be bonded to a carboxyl group or an amino group in a physiologically active substance with or without intervention of any linking aid under a mild condition to fix such physiologically active substance firmly. Therefore, it is useful as a carrier for the radioactive metallic element and the physiologically active substance.

For manufacture of the physiologically active substance-combined AAPT (I) as the non-radioactive carrier, AAPT (I) is treated with a physiologically active substance.

For manufacture of the radioactive metallic element-labeled, physiologically active substance-combined AAPT (I) as the radioactive diagnostic agent of the present invention, the AAPT (I) is usually first combined with a physiologically active substance, and then the resultant combined product is labeled with a radioactive metallic element.

The term "physiologically active substance" is intended to mean any substance which can show a specific ability to accumulate at a certain organ or tissue or a certain diseased locus or exhibits a specific behavior corresponding to a certain physiological state. Tracing of its behavior in a living body can provide information useful for diagnosis. Such physiologically active substance as having a carboxyl group or an amino group is usable advantageously in this invention. Even when a carboxyl group or an amino group is not present, it may be used by introducing previously a carboxyl group or an amino group therein. Specific examples of the physiologically active substance are blood proteins (e.g. human serum albumin, fibrinogen), enzymes (e.g. urokinase, streptokinase), hormones (e.g. thyroid stimulating hormone, parathyroid hormone), immune antibodies (e.g. IgG), antibiotics (e.g. bleomycin, kanamycin), saccharides, fatty acids, amino acids, etc.

The combination of the AAPT (I) with a physiologically active substance may be carried out according to any procedure as conventionally adopted for linking an amino group with a carboxyl group or an amino group. Examples of such procedure include the carbodiimide process, the glutaraldehyde process, etc. According to the carbodiimide process, the AAPT (I) having a primary amino group and a physiologically active substance having a carboxyl group are condensed in the presence of a carbodiimide such as 1-cyclohexyl-3-(2- morpholinyl-4-ethyl)carbodiimide or 1-ethyl-3-(3-dimethylaminopropyl)carbodiimide to form a carbonamide linkage between the amino group and the carboxyl group. According to the glutaraldehyde process, the AAPT (I) having a primary amino group and a physiologically active substance having a primary amino group are reacted in the presence of glutaraldehyde as a linking aid, and the resultant Schiff base which may or may not be isolated is reduced with a reducing agent such as sodium borohydride. In the resulting products, two amino groups are combined with intervention of a pentamethylene linkage. These bonding procedures are quite advantageous in accomplishment of the bonding under a mild condition so that any inactivation, denaturation or decomposition of the physiologically active substance does not materially take place.

When desired, the thus prepared physiologically active substance-combined (hereinafter referred to as "PAS-combined") AAPT (I) may be purified by a process known per se such as dialysis, gel filtration or column chromatography so as to eliminate impurities such as unreacted reagents therefrom. As the result, the combined product is usually obtained in the form of an aqueous solution which may be as such used for labeling with a radioactive metallic element. Alternatively, the aqueous solution may be subjected to lyophilization, evaporation under reduced pressure at low temperatures or the like to obtain a dried product, which can be also used as such or in the form of solution for labeling. Depending on the use, the said aqueous solution or the dried product may be incorporated with any additive such as a pH controlling agent (e.g. an acid, a base, a buffer), a stabilizer (e.g. ascorbic acid), an isotonizing agent (e.g. sodium chloride) or a preserving agent (e.g. benzyl alcohol). In addition, the said aqueous solution or the dried product may contain any reducing or oxidizing agent, which will act on a radioactive metallic element to be labeled so as to give a stable chelate product, as hereinafter explained. Still, the PAS-combined AAPT (I) per se is quite stable and can be readily labeled with a radioactive metallic element by a simple procedure as hereinafter explained, and therefore it may be stored and supplied on the demand so that its production from the AAPT (I) and the physiologically active substance can be saved from the practitioner such as a medical doctor.

For the labeling of the AAPT (I) or the PAS-combined AAPT (I) as the non-radioactive carrier with a radioactive metallic element, the AAPT (I) or the PAS-combined AAPT (I) may be treated with the radioactive metallic element in an appropriate form.

The term "radioactive metallic element" is intended to mean any metallic element having radioactivity, which has physical characteristics suitable for nuclear medical diagnosis. Specific examples of the radioactive metallic element are gallium-67 ($^{67}$Ga), gallium-68 ($^{68}$Ga), thallium-201 ($^{201}$Tl), $^{111}$In, $^{99m}$Tc, etc. They are normally employed in their salt forms, particularly in their water-soluble salt forms.

Depending upon the kind or state of the radioactive metallic element, there may be adopted two different labeling manners. When the radioactive metallic element is in a valency state which is not required to be reduced or oxidized for formation of a stable chelate compound, the AAPT (I) or the PAS-combined AAPT (I) is contacted with the radioactive metallic element in an aqueous medium to obtain the radioactive metallic element-labeled AAPT (I) or the radioactive metallic element-labeled, PAS-combined AAPT (I). This labeling manner may be applied to $^{67}$Ga, $^{111}$In, etc. When the radioactive metallic element is in a valency state which is required to be reduced or oxidized for formation of a stable chelate compound, the AAPT (I) or the PAS-combined AAPT (I) is contacted with the radioactive metallic element in an aqueous medium in the presence of a reducing agent or an oxidizing agent to obtain the radioactive metallic element-labeled AAPT (I) or the radioactive metallic element-labeled, PAS-combined AAPT (I). This labeling manner may be applied to $^{99m}$Tc, etc.

As the reducing agent, there may be usually employed a stannous salt, i.e. a salt of divalent tin ion ($Sn^{++}$). Specific examples are stannous halides (e.g. stannous chloride, stannous fluoride), stannous sulfate, stannous nitrate, stannous acetate, stannous citrate, etc. $Sn^{++}$ ion-bearing resins such as ion-exchange resins charged with $Sn^{++}$ ion are also usable.

When, for instance, the radioactive metallic element is $^{99m}$Tc, the AAPT (I) or the PAS-combined AAPT (I) may be treated with $^{99m}$Tc in the form of pertechnetate in an aqueous medium in the presence of a reducing agent such as a stannous salt. As to the order of the introduction of the above reagents into the reaction system, any particular limitation does not exist. Usually, however, the mixing of the stannous salt with the pertechnetate in an aqueous medium in the first place should be avoided. The stannous salt may be used in such an amount as can sufficiently reduce the pertechnetate.

The radioactive diagnostic agent should have sufficient radioactivity and radioactivity concentration which can assure reliable diagnosis. For instance, in case of the radioactive metallic element being $^{99m}$Tc, it may be included usually in an amount of 0.1 to 50 mCi in about 0.5 to 5.0 ml at the time of administration. The amount of the AAPT (I) or the PAS-combined AAPT (I) may be such as sufficient to form a stable chelate compound with the radioactive metallic element.

The thus produced radioactive metallic element-labeled AAPT (I) or radioactive metallic element-labeled, PAS-combined AAPT (I) as the radioactive diagnostic agent is sufficiently stable, and therefore it may be stored as such and supplied on the demand. When desired, the radioactive diagnostic agent may contain any additive such as a pH controlling agent (e.g. an acid, a base, a buffer), a stabilizer (e.g. ascorbic acid) or an isotonizing agent (e.g. sodium chloride).

The radioactive metallic element-labeled AAPT (I) and radioactive metallic element-labeled, PAS-combined AAPT (I) of this invention are useful for nuclear medical diagnosis. For instance, $^{99m}$Tc-labeled AAPT (I) or $^{67}$Ga-labeled AAPT (I) may be used for recording and functional measurement of myocardium. Also, for instance, $^{99m}$Tc-labeled, human serum albumin-combined AAPT (I) can be used for recording, dynamic study and quantitative measurement of the blood circulation system by administering intravenously to a human body. Further, for instance, $^{99m}$Tc-labeled, fibrinogen-combined AAPT (I) or $^{99m}$Tc-labeled, urokinase-combined AAPT (I) may be used for detection and recording of thrombosis as well as localization of thrombosis, since they accumulate at the locus of thrombosis. Furthermore, for instance, $^{99m}$Tc-labeled, streptokinase-combined AAPT (I) is useful for determination of the locus of myocardial infarction. Moreover, $^{99m}$Tc-labeled, thyroid stimulating hormone-combined AAPT (I) is useful for detection and recording of a cancer at the thyroid gland.

The radioactive diagnostic agent of this invention may be administered to a patient in an amount sufficient to produce a radioactivity necessary for examination of the organ or tissue by an appropriate route, usually through an intravenous route. For instance, the intravenous administration of a $^{99m}$Tc-labeled radioactive diagnostic agent of about 1 to 3 ml in volume having a radioactivity of about 1 to 20 mCi to a patient is quite suitable for the diagnostic purpose.

The advantages of the PAS-combined AAPT (I) as a non-radioactive carrier may be summarized as follows: (a) it is stable over a long period of time after manufacture; (b) since it can be produced under a mild condition, any unfavorable side reaction such as inactivation, denaturation or decomposition is not materially caused to the physiologically active substance; (c) any physiologically active substance having a carboxyl group or an amino group is usable as the starting material; (d) even when a carboxyl group or an amino group is not present, the introduction of such group into a physiologically active substance makes it usable as the starting material; (e) by such a simple procedure as contacting with a radioactive metallic element in an aqueous medium, it can afford a radioactive metallic element-labeled, PAS-combined AAPT (I). The advantages of the radioactive metallic element-labeled AAPT (I) as a radioactive diagnostic agent may be also summarized as follows: (a) the radioactive metallic element is completely chelated; (b) it accumulates rapidly and in high concentration in liver, kidney and especially in myocardium; (c) it can be prepared by extremely simple process. Likewise, the advantages of the radioactive metallic element-labeled, PAS-combined AAPT (I) as a radioactive diagnostic agent may be summaried as follows: (a) it is stable over a long period of time after manufacture; (b) the labeling efficiency with the radioactive metallic element is extremely high (nearly 100%); (c) since the labeling operation is quite simple, any unfavorable side reaction such as inactivation, denaturation or decomposition is not caused to the physiologically active substance bonded to the AAPT (I); (d) among various radioactive metallic elements, the most suitable one for the diagnostic purpose may be chosen and used so that the informations for diagnosis is enhanced not only in quantity but also in quality with reduction of the exposure dose.

Practical and presently preferred embodiments of the invention are illustratively shown in the following Examples wherein % is by weight, unless otherwise defined.

EXAMPLE 1

Preparation of 1-(p-N,N-dimethylaminoethyl)phenylpropane-1,2-dione bis(4-methylthiosemicarbazone) (hereinafter referred to as "DEPM"):

(a) Anhydrous aluminium chloride (66 g) was added to a solution of N,N-dimethylphenethylamine (22.358 g) in dried carbon disulfide (225 ml). Then, propionyl chloride (15.27 g) was added dropwise to the solution at 50° to 60° C. with stirring over a period of about 1 hour and the solution was refluxed with stirring for 4.5 hours. Cold water was added to the solution to decompose the aluminium chloride. The solution was adjusted to weak alkaline with sodium hydroxide solution and extracted with ethyl ether. The ethereal extract was dried over anhydrous sodium sulfate, concentrated and distilled under reduced pressure to give p-N,N-dimethylaminoethylpropiophenone (25 g, 81%) as a fraction boiling at 115°–117° C./1–2 mmHg.

(b) Dried hydrogen chloride was bubbled into a solution of p-N,N-dimethylaminoethylpropiophenone (2.33 g) obtained in (a) in absolute ethanol (75 ml). Isopropyl nitrite (1.07 g) was added to the solution, which was stirred overnight at room temperature. The ethanol was removed by distillation from the solution to give crude product, which was recrystallized from ethanol to give p-N,N-dimethylaminoethyl-2-hydroxyiminopropiophenone in an approximately theoretical yield.

M.P.: 220°–222° C. (hydrochloride); 186°–188° C. (free base).

Analysis: Calcd. (%): C, 57.93; H, 7.28; N, 10.56. Found: C, 57.67; H, 7.07; N, 10.35.

(c) A solution of p-N,N-dimethylaminoethyl-2-hydroxyiminopropiophenone (2.34 g) obtained in (b) and 4-methylthiosemicarbazide (2.31 g) in 90% ethanol (12 ml) was adjusted to pH 2 with conc. hydrochloric acid and refluxed with stirring for 8 hours. After cooling, produced crystals were collected and recrystallized from ethanol to give DEPM (1.0 g, 25%).

M.P.: 230°–232° C. (hydrochloride).

Analysis: Calcd. (%): C, 47.36; H, 6.65; N, 22.64. Found: C, 47.48; H, 6.56; N, 22.80.

EXAMPLE 2

Preparation of 1-(p-aminomethyl)phenylpropane-1,2-dione bis(4-methylthiosemicarbazone) (hereinafter referred to as "AMPM"):

A solution of p-aminomethyl-2-hydroxyiminopropiophenone (2.06 g) and 4-methylthiosemicarbazide (2.31 g) in ethanol (10 ml) was adjusted to pH 2 with conc. hydrochloric acid and refluxed with stirring for 7 hours. After cooling, produced crystals were collected and recrystallized from ethanol to give AMPM (1.1 g, 31%).

Analysis (hydrochloride): Calcd. (%): C, 41.40; H, 5.88; N, 24.21. Found: C, 41.45; H, 5.96; N, 24.16.

EXAMPLE 3

Preparation of 1-(p-aminoethyl)phenylpropane-1,2-dione bis(4-methylthiosemicarbazone) (hereinafter referred to as "AEPM"):

(a) To a solution of phenethylamine (12.2 g) in pyridine (30 ml) was added trifluoroacetic anhydride (15 ml). The solution was stirred at room temperature for 12 hours and then distilled under reduced pressure to give N-trifluoroacetylphenethylamine (16.5 g, 75%) as a fraction distilling at 103°–104° C./4 mmHg.

(b) Anhydrous aluminium chloride (22 g) was added to a solution of N-trifluoroacetylphenethylamine (11.0 g) obtained in (a) in dried carbon disulfide (75 ml). Then, propionyl chloride (5.1 g) was added dropwise to the solution with stirring. The solution was refluxed with stirring for 4.5 hours and allowed to stand overnight. Cold water was added to the solution to decompose the aluminium chloride. The solution was adjusted to weak alkaline with sodium hydroxide solution and extracted with ethyl acetate. The extract was dried over anhydrous sodium sulfate and concentrated to give black residue, which was dissolved in hot methanol, treated with activated charcoal and cooled to give p-N-trifluoroacetamidoethylpropiophenone (3.34 g, 24.5%).

(c) Potassium carbonate (2.9 g) was added to a solution of p-N-trifluoroacetamidoethylpropiophenone (2.73 g) in a mixture of methanol (30 ml) and water (12 ml) and the solution was stirred overnight. The potassium carbonate was decomposed with addition of 5% hydrochloric acid. Then, the solution was made alkaline with 10% sodium hydroxide and extracted with ethyl ether. The extract was dried over anhydrous sodium sulfate. Gaseous hydrogen chloride was bubbled into the extract to give crystals of p-aminoethylpripiophenone hydrochloride in an approximately theoretical yield.

Analysis: Calcd. (%): C, 74.36; H, 8.60; N, 7.84. Found: C, 74.54; H, 8.53; N, 7.90.

(d) Dried hydrogen chloride was bubbled into a solution of p-aminoethylpripiophenone hydrochloride (2.14 g) in absolute ethanol (50 ml). Isopropyl nitrite (1.07 g) was added to the solution, which was stirred overnight at room temperature. The solvent was removed by distillation to give crude product, which was recrystallized from ethanol to give p-aminoethyl-2-hydroxyiminopropiophenone in an approximately theoretical yield.

(e) A solution of p-aminoethyl-2-hydroxyiminopropiophenone (1.22 g) obtained in (d) and 4-methylsemicarbazide (1.6 g) in 90% ethanol (10 ml) was adjusted to pH 2 and refluxed with stirring for 7.5 hours. After cooling, produced crystals were collected and recrystallized from ethanol to give AEPM (0.65 g, 30%).

Analysis: Calcd. (%): C, 49.46; H, 6.50; N, 26.30; S, 17.74. Found: C, 49.29; H, 6.34; N, 26.83; S, 17.54.

EXAMPLE 4

Preparation of a carrier composition for radioactive diagnostic agent containing DEPM:

A mixture of DEPM (3.9 mg), 1N sodium hydroxide solution (1 ml), 0.1M acetate buffer (pH, 6.0) (3 ml) and 1N hydrochloric acid (1 ml) was prepared and allowed to stand until clear solution was obtained. All the procedures were carried out in an aseptic condition.

EXAMPLE 5

Preparation of a carrier composition containing stannous chloride:

The solution (1 ml) obtained in Example 4 was mixed with a solution (0.1 ml) of stannous chloride (0.15 mg/ml) and the mixture was shaken for a brief period to obtain a clear solution. The solution was stored in a stoppered container, the air in which was replaced by nitrogen gas.

EXAMPLE 6

Preparation of a carrier composition containing stannous ion charged on ion-exchange resin:

The solution (1 ml) obtained in Example 4 was mixed with ion-exchange resin (Dowex 50W×8, 3 mg) absorbing stannous ion (5.5 μg $Sn^{+2}$/mg resin). The mixture was shaken for a brief period and stored in a stoppered container, the air in which was replaced by nitrogen gas. All the procedures were carried out in an aseptic condition.

EXAMPLE 7

Preparation of $^{67}$Ga-labeled radioactive diagnostic agent containing DEPM:

The solution (1 ml) obtained in Example 4 was mixed with gallium ($^{67}$Ga) chloride solution (10 mCi/ml, 1 mCi) and the mixture was shaken for a brief period to give a $^{67}$Ga-labeled radioactive diagnostic agent. The procedures were carried out aseptically. The agent gave a single radioactive spot at Rf=0.55 in silica gel thin layer chromatography (solvent, 10% ammonium acetate:methanol=1:1), proving that the radioactive gallium was completely chelated.

EXAMPLE 8

Preparation of $^{99m}$Tc-labeled radioactive diagnostic agent containing DEPM:

Commercial pertechnetate ($^{99m}$Tc) solution (1 mCi/ml, 1 mCi) was added to the carrier composition obtained in Example 6 and the mixture was moved slowly for about 3 minutes. Then, the ion-exchange resin was removed by filtration to obtain $^{99m}$Tc-labeled radioactive diagnostic agent.

EXAMPLE 9

Physical properties of $^{99m}$Tc-labeled radioactive diagnostic agent containing DEPM:

The physical properties of the $^{99m}$Tc-labeled radioactive diagnostic agent obtained in Example 8 were evaluated.

(1) pH=6.0.

(2) Silica gel TLC

A single radioactive peak was detected at Rf=0.53–0.57 on scanning a chromatogram of the labeled agent developed with an isometric mixture of 10% ammonium acetate and methanol by means of a chromatogram-scanner. Since the pertechnetate ion ($^{99m}$Tc) is known to have an Rf value of 0.91 in the same chromatographic system, it was proved that the technetium-99m atom was completely chelated.

(3) Electrophoresis

The labeled agent was submitted to electrophoresis in 0.1M phosphate buffer (pH, 7.0) at the potential difference of 500 V for 1 hour using a sheet of filter paper as electrophoretic membrane. A single radioactive peak was detected at 0.9–1.0 cm in the negative side on scanning the air-dried membrane using chromatogram-scanner. Since the pertechnetate ($^{99m}$Tc) ion is known to move 5.7–6.0 cm in the positive direction, it was proved by the above electrophoresis that the technetium-99m atom was completely chelated and the chelated ion carries the positive charge.

EXAMPLE 10

Behaviors of $^{99m}$Tc-labeled radioactive diagnostic agent containing DEPM in mice:

Each portion (0.1 ml) of the $^{99m}$Tc-labeled radioactive diagnostic agent prepared in Example 8 was administered intravenously to mice (a group of three male animals) at the tail vein, which were sacrificed at fixed times and radioactivity in each of organs was evaluated. Changes with passage of time for distribution of radioactivity per unit weight of organs together with standard deviations are shown in the following Table.

TABLE 1

| | Variation of blood level in mice (%/g) | | |
| --- | --- | --- | --- |
| | Time for administration (hours) | | |
| Organs | 0.5 | 1 | 3 |
| Blood | 1.16 ± 0.27 | 0.46 ± 0.10 | 0.18 ± 0.02 |
| Liver | 16.26 ± 3.59 | 12.46 ± 1.95 | 17.11 ± 3.92 |
| Kidneys | 3.36 ± 0.37 | 2.73 ± 0.23 | 1.77 ± 0.32 |
| Myocardium | 2.58 ± 0.07 | 1.33 ± 0.15 | 0.72 ± 0.22 |
| Myocardium/Blood | 2.22 | 2.89 | 4.00 |

From the above result, it can be clearly seen that the radioactive diagnostic agent of the invention accumulates rapidly and in high concentration in liver, kidneys and myocardium. Especially, the accumulation in myocarbium is comparative to that of thallium ($^{201}$Tl) chloride which is commonly used. In addition, myocardium/blood ratio is more than 2 and proved to be well usable in nuclear medical diagnosis for the purpose of recording, dinamic study and functional test of myocardium.

EXAMPLE 11

Behaviors of $^{67}$Ga-labeled radioactive diagnostic agent containing DEPM in mice:

Almost the same result as that in Example 10 was obtained in an experiment using the $^{67}$Ga-labeled radioactive diagnostic agent prepared in Example 7.

EXAMPLE 12

Toxicity of $^{67}$Ga- or $^{99m}$Tc-labeled diagnostic agents containing DEPM:

The radioactive diagnostic agents prepared in Examples 7 and 8 were subjected to attenuation of the radioactivity to an appropriate extent. Each of the resultant products were administered intravenously to groups of male and female rats of SD strain, each group consisting of 5 animals, at a dose of 1 ml per 100 grams of the body weight (corresponding to 300 times the expected dose to human beings) and also to groups of male and female mice of ICR strain, each group consisting of 5 animals, at a dose of 0.5 ml per 10 grams of the body weight (corresponding to 1500 times the expected dose to human beings). As the control, the same volume of a physiological saline solution as above was intravenously administered to the separate groups of the same animals as above. The animals were fertilized for 10 days, and the variation in the body weight was recorded every day. No significant difference was recognized between the medicated groups and that of the control. After 10 days from the administration, all the animals were sacrificed and inspected for the abnormality in various organs. However, no abnormality was observed in any of the animals.

It can be safely said from the above results that the toxicity of the radioactive diagnostic agent according to the invention is extremely low.

EXAMPLE 13

Preparation of human serum albumin-combined AEPM as a non-radioactive carrier:

Human serum albumin (lyophilized; 75 mg) was dissolved in water (5 ml) to give a solution which is hereinafter referred to as "solution (A)". Separately, AEPM was dissolved in dimethylformamide to a concentration of 5 mg/ml. The resultant solution (0.5 ml) was added to the solution (A). The mixture thus formed is hereinafter referred to as "solution (B)". The solution (B) was adjusted to pH 4.6 with 0.1N hydrochloric acid. An aqueous solution of 1-ethyl-3-(3-dimethylaminopropyl)carbodiimide hydrochloride (10 mg/ml; 1.3 ml) was added to the solution (B) and adjusted with 0.1N hydrochloric acid to pH 4.6, followed by stirring at a temperature below 5° C. for about 10 hours. The resultant mixture was admitted in a dialyzing tube and subjected to dialysis in a conventional manner for 24 hours, followed by centrifugation and lyophilization to give the human serum albumin-combined AEPM as white crystals. The crystals (67 mg) were dissolved in 0.2M acetate buffer (pH, 2.64; 5 ml), in which dissolved oxygen was replaced previously with nitrogen, and 0.1 mM aqueous stannous chloride solution (2.0 ml) and ascorbic acid (1.2 mg) were added thereto. The resultant solution was passed through a filter having a pore size of 0.22 μm, and each of 1.5 ml portions of the filtrate was filled in a vial, the inside of which was flushed with nitrogen, to obtain a non-radioactive carrier as a slightly pale yellow, transparent solution. The above operations were effected under sterile conditions.

EXAMPLE 14

Preparation of human serum albumin-combined AMPM as a non-radioactive carrier:

AMPM (5 mg) was dissolved in dimethylformamide (2 ml), an equimolar amount of glutaraldehyde to AMPM was added thereto, and the resultant mixture was stirred at room temperature for 15 minutes to make the solution (A). Separately, human serum albumin (lyophilized; 100 mg) was dissolved in 0.01M phosphate buffer-0.15M sodium chloride solution (pH, 7.4; 10 ml) to make the solution (B). The solution (A) (1.0 ml) was added to the solution (B) with ice cooling, and the resultant mixture was stirred at the same temperature as above for about 0.5 hour. After addition of sodium borohydride (1 mg), stirring was continued at a temperature of 0° to 4° C. for about 1 hour, whereby reduction proceed. The resultant mixture was admitted in a dialyzing tube and subjected to dialysis in a conventional manner for 24 hours. The resulting solution was passed through a filter having a pore size of 0.22 μm, and each of 1.0 ml portions of the filtrate was filled in a vial, followed by lyophilization to obtain a non-radioactive carrier. The above operations were effected under sterile conditions.

When dissolved in water, the non-radioactive carrier gave a slightly pale yellow, transparent solution.

EXAMPLE 15

Preparation of urokinase-combined AMPM as a non-radioactive carrier:

Cooling on an ice bath, purified urokinase (lyophilized; 50 mg) was dissolved in water (5 ml) to give the solution (A). Separately, AMPM was dissolved in dimethylformamide to a concentration of 5 mg/ml. The resultant solution (0.5 ml) was added to the solution (A), and the pH was adjusted with 0.1N hydrochloric acid to about 4.6 to make the solution (B). To the solution (B) was added an aqueous solution of 1-cyclohexyl-3-(2-morpholinyl-4-ethyl)carbodiimide (50 mg/ml; 1.5 ml), and the resultant mixture was adjusted with 0.1N hydrochloric acid to a pH of about 4.6, followed by stirring at a temperature below 5° C. for about 2 hours. The reaction mixture was chromatographed on Sephadex G-50 (2×30 cm column) and eluted with 0.01M phosphate buffer-0.15M sodium chloride solution (pH, 7.4). The eluate was diluted with 0.01M phosphate-0.15M sodium chloride solution to a concentration of 5.0 mg/ml of urokinase. The dilution was passed through a filter having a pore size of 0.22 μm, and each of 1.5 ml portions of the filtrate was filled in a vial to obtain a non-radioactive carrier as a slightly pale yellow transparent solution. The above operations were effected under sterile conditions.

EXAMPLE 16

Preparation of $^{99m}$Tc-labeled, human serum albumin-combined AEPM as a radioactive diagnostic agent:

The human serum albumin-combined AEPM (solution) obtained in Example 13 (1.0 ml) was admixed with a physiological saline solution (0.5 ml) containing $^{99m}$Tc (3 mCi) in the form of pertechnetate, followed by stirring sufficiently to give an aqueous solution containing the $^{99m}$Tc-labeled, human serum albumin-combined AEPM useful as a radioactive diagnostic agent. This solution was pale yellow, transparent and had a pH around 3.0.

EXAMPLE 17

Preparation of $^{67}$Ga-labeled, human serum albumin-combined AMPM as a radioactive diagnostic agent:

The human serum albumin-combined AMPM (lyophilized) obtained in Example 14 was dissolved in 0.2M acetate buffer (pH, 4.0; 1.0 ml), and 0.01N hydrochloric acid (0.5 ml) containing $^{67}$Ga (2 mCi) in the form of gallium chloride was added thereto to give an aqueous solution containing the $^{67}$Ga-labeled, human serum albumin-combined AMPM useful as a radioactive diagnostic agent. This solution was slightly pale yellow, transparent and had a pH around 3.7.

EXAMPLE 18

Properties of $^{99m}$Tc-labeled, human serum albumin-combined AEPM as a radioactive diagnostic agent:

In order to examine the labeling efficiency of the $^{99m}$Tc-labeled, human serum albumin-combined AEPM obtained in Example 16, its aqueous solution was subjected to thin layer chromatography using silica gel as a retention material and methylethylketone as a developing solvent, and scanning was carried out by the use of a radiochromato-scanner. The radioactivity was recorded as a single peak at the original point. No peak due to a radioactive impurity such as free pertechnetate ion (Rf=1.0) was observed.

Then, the $^{99m}$Tc-labeled, human serum albumin-combined AEPM obtained in Example 16 was subjected to electrophoresis (1.7 mA/cm; 15 minutes) using a Veronal buffer (pH, 8.6) as a developing solvent and a cellulose acetate membrane as an electrophoretic membrane, and scanning was effected by the use of a radiochromato-scanner. The radioactivity was recognized as a single peak at the locus 1.8 cm distant from the original line to the positive side. This locus was the same as that of the coloring band of human serum albumin with Ponceau 3R.

From the above results, it may be said that the $^{99m}$Tc-labeled, human serum albumin-combined AEPM according to the invention has a labeling efficiency of nearly 100%, and its electric charge is substantially the same as that of human serum albumin.

EXAMPLE 19

Behaviors of $^{99m}$Tc-labeled, human serum albumin-combined AEPM in rats:

The $^{99m}$Tc-labeled, human serum albumin-combined AEPM obtained in Example 16 (1.0 ml) was administered intravenously to each of female rats of SD strain at the tail vein, and the variation of the blood level with the lapse of time was recorded. For the control, the same examination as above was carried out by the use of conventional $^{99m}$Tc-labeled, human serum albumin and conventional $^{131}$I-labeled, human serum albumin.

The results are shown in Table 2 wherein the blood level at each measuring time is indicated by an absolute value (% of dose/g; in average).

TABLE 2

| | Variation of blood level in rats (%/g) | | | |
|---|---|---|---|---|
| | Time after administration (hours) | | | |
| Agent tested | 0.5 | 1 | 2 | 3 |
| $^{99m}$Tc-labeled, human serum albumin-combined AMPM of the invention | 7.43 | 7.00 | 6.22 | 5.14 |
| Conventional $^{99m}$Tc-labeled, human serum albumin (Commercial product A) | 3.95 | 3.68 | — | 2.51 |
| Conventional $^{99m}$Tc-labeled, human serum albumin (Commercial product B) | 3.15 | 2.16 | — | 1.88 |
| Conventional $^{131}$I-labeled, human serum albumin | 5.93 | 5.64 | — | 4.59 |

From the above results, it is understood that the $^{99m}$Tc-labeled, human serum albumin-combined AEPM can maintain a remarkably high blood level for a long period of time in comparison with conventional $^{99m}$Tc-labeled, human serum albumin and conventional $^{131}$I-labeled, human serum albumin. It is also understood that the $^{99m}$Tc-labeled, human serum albumin-combined AEPM is quite stable in a living body. Thus, the $^{99m}$Tc-labeled, human serum albumin-combined AEPM is quite suitable for the use in nuclear medical diagnosis aiming at recording, dynamic study and quantitative measurement of the blood circulation system.

EXAMPLE 20

Properties of $^{67}$Ga-labeled, human serum albumin-combined AMPM as a radioactive diagnostic agent:

In order to examine the labeling efficiency of the $^{67}$Ga-labeled, human serum albumin-combined AMPM obtained in Example 17, it was subjected to electrophoresis (1.7 mA/cm; 15 minutes) using a Veronal buffer (pH, 8.6) as a developing membrane, and scanning was effected by the use of a radiochromato-scanner. The radioactivity was recognized as a single peak at the locus 1.8 cm distant from the original line to the positive side. This locus was the same as that of the coloring band of human serum albumin with Ponceau 3R.

From the above results, it may be said that the $^{67}$Ga-labeled, human serum albumin-combined AMPM according to the invention has a labeling efficiency of nearly 100%, and its electric charge is substantially the same as that of human serum albumin.

EXAMPLE 21

Properties of non-radioactive urokinase-combined AMPM:

The enzymatic activity of the non-radioactive urokinase-combined AMPM obtained in Example 15 was measured by the ester decomposition process using N-α-acetyl-L-lysine methyl ester to be substantially the same as purified urokinase used as the starting material.

From the above results, it may be said that the non-radioactive urokinase-combined AMPM retains the enzymatic activity of the starting purified urokinase. In addition, $^{111}$In-labeled urokinase-combined AMPM retained substantially the enzymatic activity showing no material difference from urokinase itself in the behavior in a living body.

EXAMPLE 22

Stability of human serum albumin-combined AEPM:

The human serum albumin-combined AEPM obtained in Example 13 was stored in a refrigerator at 4° to 8° C. for 30 days and then treated with $^{99m}$Tc according to the procedure as in Example 16 to give an aqueous solution containing the $^{99m}$Tc-labeled, human serum albumin-combined AEPM. With this solution, thin layer chromatography and electrophoresis were carried out according to the procedure as in Example 18 and also behaviors in rats were examined according to the procedure as in Example 19. The results were substantially the same as in Examples 18 and 19. Thus, it may be said that no material change is produced in the human serum albumin-combined AEPM by the storage for 30 days.

EXAMPLE 23

Stability of human serum albumin-combined AMPM:

The human serum albumin-combined AMPM obtained in Example 14 was stored in a refrigerator at 4° to 8° C. for 30 days and then treated with $^{67}$Ga according to the procedure as in Example 17 to give an aqueous solution containing $^{67}$Ga-labeled, human serum albumin-combined AMPM. With this solution, electrophoresis was carried out according to the procedure as in Example 20. The radioactivity was recognized as a single peak, and its locus was confirmed to be the same as that of human serum albumin by coloring with Ponceau 3R. Thus, it may be said that no material change is produced in the human serum albumin-combined AMPM by the storage for 30 days.

EXAMPLE 24

Stability of $^{99m}$Tc-labeled, human serum albumin-combined AEPM:

An aqueous solution containing the $^{99m}$Tc-labeled, human serum albumin-combined AEPM obtained in Example 16 was stored at room temperature (24°–27° C.) for 36 hours. With this solution, thin layer chromatography and electrophoresis were carried out according to the procedure as in Example 18 and also behaviors in rats were examined according to the procedure as in Example 19. The results were substantially the same as in Examples 18 and 19. Thus, it may be said that no material change is produced in the $^{99m}$Tc-labeled, human serum albumin-combined AEPM by the storage for 36 hours.

EXAMPLE 25

Stability of $^{67}$Ga-labeled, human serum albumin-combined AMPM:

An aqueous solution containing the $^{67}$Ga-labeled, human serum albumin-combined AMPM obtained in Example 17 was stored at room temperature (24°–27° C.) for 72 hours. With this solution, electrophoresis was carried out according to the procedure as in Example 20. The radioactivity was recognized as a single peak, and its locus was confirmed to be substantially the same as that of human serum albumin by coloring with Ponceau 3R. Thus, it may be said that no material change is produced in the $^{67}$Ga-labeled, human serum albumin-combined AMPM by the storage for 72 hours.

EXAMPLE 26

Toxicity of non-radioactive carriers:

The non-radioactive carriers obtained in Examples 13 to 15 (perfectly dissolved in 0.2M acetate buffer in case of the non-radioactive carrier obtained in Example 14) were administered intravenously to groups of male and female rats of SD strain, each group consisting of 5 animals, at a dose of 1 ml per 100 grams of the body weight (corresponding to 600 times the expected dose to human beings) and also to groups of male and female mice of ICR strain, each group consisting of 5 animals, at a dose of 0.5 ml per 10 grams of the body weight (corresponding to 3000 times the expected dose to human beings). As the control, the same volume of a physiologically saline solution as above was intravenously administered to the separate groups of the same animals as above.

The animals were fertilized for 10 days, and the variation in body weight during that period was recorded every day. No significant difference was recognized between the medicated groups and that of the control.

After 10 days from the administration, all the animals were sacrificed and subjected to observation of the abnormality in various organs. But, no abnormality was seen in any of the animals.

From the above results, it may be said that the toxicity of the non-radioactive carriers of the invention is extremely low.

EXAMPLE 27

Toxicity of the radioactive diagnostic agent:

The $^{99m}$Tc-labeled, human serum albumin-combined AEPM obtained in Example 16 was subjected to attenuation of the radioactivity to an appropriate extent, and the resultant product was subject to test for toxicity in the same manner as in Example 26. No significant difference was recognized between the medicated groups and the control groups. In all of the animals sacrificed after 10 days from the administration, no abnormality was observed in their organs. Thus, it may be said that the radioactive diagnostic agent of the invention does not produce any material toxicity in tested animals even when administered in such a large dose as corresponding to 400 to 2000 times the expected dose to human beings.

What is claimed is:

1. A compound of the formula:

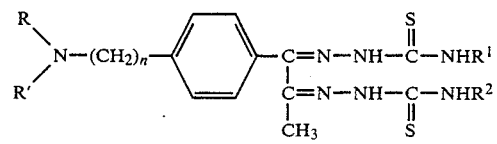

wherein R, R', R$^1$ and R$^2$ are each a hydrogen atom or a C$_1$–C$_3$ alkyl group and n is an integer of 1 to 3.

2. The compound according to claim 1, wherein R$^1$ and R$^2$ are each methyl.

3. The compound according to claim 2, wherein R and R' are each methyl and n is 2.

4. The compound according to claim 2, wherein R and R' are each hydrogen and n is 1.

5. The compound according to claim 2, wherein R and R' are each hydrogen and n is 2.

6. A radioactive metallic element-combined compound comprising the compound according to claim 1 and a radioactive metallic element bound with said compound through a chelating bond.

7. A non-radioactive composition for a radioactive metallic element comprising the compound according to claim 1 and a physiologically acceptable carrier or diluent.

8. The non-radioactive composition according to claim 7, which contains a reducing agent.

9. A radioactive diagnostic composition comprising the radioactive metallic element-combined compound according to claim 6 and a physiologically acceptable carrier or diluent.

10. A physiologically active substance-combined compound comprising the compound according to claim 1 and a physiologically active substance bonded therewith by a chemical bond.

11. A radioactive metallic element-combined compound comprising a compound of the formula:

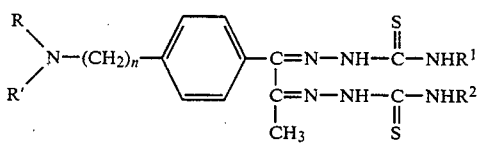

wherein R, R', R¹ and R² are each a hydrogen atom or a $C_1$–$C_3$ alkyl group and n is an integer of 0 to 3; and a radioactive metallic element bound with said compound through a chelating bond.

12. The radioactive metallic element-combined compound according to claim 11, wherein the radioactive metallic element is $^{99m}Tc$.

13. The radioactive metallic element-combined compound according to claim 11, wherein the radioactive metallic element is $^{67}Ga$.

14. A non-radioactive composition for a radioactive metallic element comprising a compound of the formula:

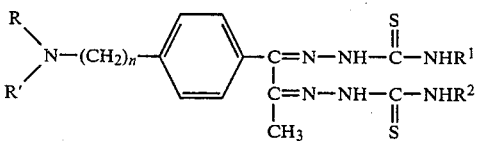

wherein R, R', R¹ and R² are each a hydrogen atom or a $C_1$–$C_3$ alkyl group and n is an integer of 0 to 3; a reducing agent; and a physiologically acceptable carrier or diluent.

15. The non-radioactive composition according to claim 14, wherein the reducing agent is a stannous salt.

16. The non-radioactive composition according to claim 15, wherein the stannous salt is charged on ion-exchange resin.

17. A radioactive diagnostic composition, comprising a compound of the formula:

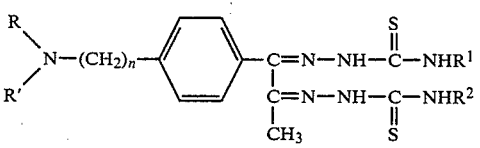

wherein R, R', R¹ and R² are each a hydrogen atom or a $C_1$–$C_3$ alkyl group and n is an integer of 0 to 3; a radioactive metallic element bound with said compound through a chelating bond; and a physiologically acceptable carrier or diluent.

18. A physiologically active substance-combined compound comprising a compound of the formula:

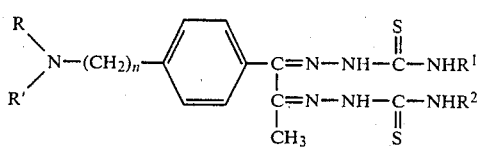

wherein R, R', R¹ and R² are each a hydrogen atom or a $C_1$–$C_3$ alkyl group and n is an integer of 0 to 3; and a physiologically active substance bonded therewith by a chemical bond.

19. The physiologically active substance-combined compound according to claim 18, wherein the chemical bond is a carbonamide linkage.

20. The physiologically active substance-combined compound according to claim 18, wherein the chemical bond is a pentamethylene linkage.

21. The physiologically active substance-combined compound according to claim 18, wherein the physiologically active substance is human serum albumin.

22. The physiologically active substance-combined compound according to claim 18, wherein the physiologically active substance is urokinase.

23. A radioactive metallic element-labeled, physiologically active substance-combined compound comprising the physiologically active substance-combined compound of claim 18, and a radioactive metallic element bound with said compound through a chelating bond.

24. The radioactive metallic element-labeled, physiologically active substance-combined compound according to claim 23, wherein the radioactive metallic element is $^{99m}Tc$.

25. The radioactive metallic element-labeled, physiologically active substance-combined compound according to claim 23, wherein the radioactive metallic element is $^{67}Ga$.

26. A non-radioactive composition comprising the physiologically active substance-combined compound according to claim 18 and a physiologically acceptable carrier or diluent.

27. The non-radioactive composition according to claim 26, which is in the form of solution.

28. The non-radioactive composition according to claim 26, which is in the form of lyophilized powder.

29. A radioactive diagnostic composition, comprising: the radioactive metallic element-labeled, physiologically active substance-combined compound according to claim 23 and a physiologically acceptable carrier or diluent.

30. A diagnostic method comprising the steps of: administering an effective imaging amount of the composition of claim 29 to a subject to be diagnosed; and imaging said subject.

31. A process for preparing a physiologically active substance-combined compound which comprises reacting a compound of the formula:

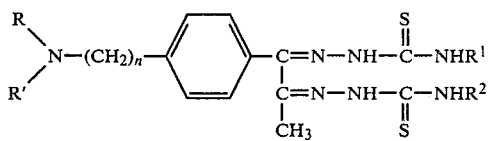

wherein R, R', $R^1$ and $R^2$ are each a hydrogen atom or a $C_1$-$C_3$ alkyl group and n is an integer of 0 to 3 with a physiologically active substance.

32. The process according to claim 31, wherein the physiologically active substance has a carboxyl group, and the reaction proceeds between the amino group in said compound and the carboxyl group in the physiologically active substance to form a carbonamide linkage.

33. The process according to claim 31, wherein the physiologically active substance has an amino group, and the reaction proceeds between the amino group in said compound and the amino group in the physiologically active substance in the presence of glutaraldehyde, followed by reduction to form a pentamethylene linkage between the said amino groups.

34. A process for preparing a radioactive metallic element-labeled, physiologically active substance-combined compound, which comprises contacting the physiologically active substance-combined compound according to claim 18 with a radioactive metallic element to combine them through a chelating bond.

35. The process according to claim 34, wherein the contact is carried out in an aqueous medium.

* * * * *